US006511819B2

(12) United States Patent
Tryland et al.

(10) Patent No.: US 6,511,819 B2
(45) Date of Patent: Jan. 28, 2003

(54) RAPID COLIFORM DETECTION SYSTEM

(75) Inventors: Ingun Tryland, Oslo (NO); James D. Berg, Oslo (NO); Kari Skjanes, Oslo (NO)

(73) Assignee: Nye Colifast AS

( * ) Notice: Subject to any disclaimer, the term of this patent is extended or adjusted under 35 U.S.C. 154(b) by 0 days.

(21) Appl. No.: 09/821,659

(22) Filed: Mar. 29, 2001

(65) Prior Publication Data

US 2001/0051355 A1 Dec. 13, 2001

Related U.S. Application Data

(63) Continuation-in-part of application No. 09/643,437, filed on Aug. 22, 2000, now abandoned, which is a continuation of application No. 09/373,401, filed on Aug. 12, 1999, now Pat. No. 6,165,742, which is a continuation of application No. 09/143,266, filed on Aug. 28, 1998, now Pat. No. 5,972,641.

(51) Int. Cl.$^7$ .............................. C12Q 1/04; C12Q 1/02; C12Q 1/54; C12Q 1/22
(52) U.S. Cl. .............................. 435/34; 435/29; 435/14; 435/38; 435/31; 435/968
(58) Field of Search .............................. 435/34, 29, 14, 435/38, 31, 968

(56) References Cited

U.S. PATENT DOCUMENTS

| | | | |
|---|---|---|---|
| 3,928,139 A | 12/1975 | Dorn | 195/103.5 |
| 4,242,447 A | 12/1980 | Findl et al. | 435/39 |
| 4,289,498 A | 9/1981 | Baughman et al. | 23/230 |
| 4,340,671 A | 7/1982 | Gibson | 435/32 |
| 4,587,213 A | 5/1986 | Malecki | 435/39 |
| 4,591,554 A | 5/1986 | Koumura et al. | 435/18 |
| 4,693,972 A | 9/1987 | Mansour et al. | 435/34 |
| 4,777,137 A | 10/1988 | Lemonnier | 435/299 |
| 4,923,804 A | 5/1990 | Ley et al. | 435/38 |
| 4,925,789 A | 5/1990 | Edberg | 435/38 |
| 5,292,644 A | 3/1994 | Berg | 435/29 |
| 5,429,933 A | 7/1995 | Edberg | 435/34 |
| 5,518,894 A | 5/1996 | Berg | 435/34 |
| 5,541,082 A | 7/1996 | Botchner | 435/34 |
| 5,550,032 A | 8/1996 | Isbister | 435/39 |
| 5,610,029 A | 3/1997 | Ehrenfeld et al. | 435/34 |
| 5,612,186 A | 3/1997 | Huang et al. | 435/37 |
| 5,620,865 A | 4/1997 | Chen et al. | 435/34 |
| 5,633,144 A | 5/1997 | Bitton et al. | 435/38 |
| 5,663,057 A | 9/1997 | Drocourt et al. | 435/40 |
| 5,726,031 A | 3/1998 | Roth et al. | 435/34 |
| 5,780,259 A | 7/1998 | Edberg | 435/34 |
| 5,972,641 A | * 10/1999 | Ofjord et al. | 435/34 |
| 6,165,742 A | * 12/2000 | Ofjord et al. | 435/34 |

FOREIGN PATENT DOCUMENTS

| | | |
|---|---|---|
| WO | 8605206 | 9/1986 |
| WO | 9614431 | 11/1995 |
| WO | 9640980 | 5/1996 |
| WO | 9718455 | 11/1996 |
| WO | 9811252 | 9/1997 |

OTHER PUBLICATIONS

W.R. Bailey, E.G. Scott (1966) Staining Formulae and Procedures, Chapter 37, in *Diagnostic Microbiology,* Mosby Co., St. Louis, pp. 318–319.
*Standard Methods for the Examination of Water and Wastewater,* Seventeen Ed., 1989, American Public Health Association, Washington, D.C., pp. 9–80 to 9–97.
G.G. Geesey, (Nov. 1987) Survival of Microorganisms in Low Nutrient Waters, Chapter 1, in *Biological Fouling of Industrial Waste Water Systems: A Problem Solving Approach,* Water Micro Associates, California, M.W. Mittleman and G.G. Geesey eds., pp. 1–23.
"ColiQuik" Coliform Detection Method of Hach Chemical Co., pp. 112, 113, 119 of Hach Catalog.
"Colifast" Coliform Monitoring Method by Palintest (Brochure), p. 20., Feb. 1990.
B.H. Olson, D.L. Clark, B.B. Milner, M.H. Stewart, and R.L. Wolfe, "Total Coliform Detection in Drinking Water: Comparison of Membrane Filtration with Colilert and Coliquik", *Appl. Env. Micro.,* 57:1535–1539, May 1991.
S. Stratman, "Rapid Specific Environment Coliform Monitoring", *International Laboratory,* pp. 40–43, Dec. 1988.
"Research Applications: Proven Utility Benefits", *AWWA Research Foundation,* No. 4, May 1993.
Idexx Environmental Products Catalog, Idexx Laboratories, Inc. Westbrook, Maine, 1995, 4 pages.
Palintest Colilert Brochure, Palintest Ltd., England, 4 pages.
Colilert, The Breakthrough in Coliform and *E. coli* Testing, Brochure, Idexx Laboratories, Westbrook, Maine, Nov. 1993, 4 pages.
Snyder et al., "Pattern Recognition Analysis of In Vivo Enzyme–Substrate Fluorescence Velocities in Microorganism Detection and Identification", *Applied and Environmental Microbiology,* May 1986, pp. 969–977.
Maddocks et al., Technical Method. A Rapid Method For Identifying Bacterial Enzymes:, *The Journal of the Association of Clinical Pathologists,* 28(8):686, Aug. 1975.

* cited by examiner

*Primary Examiner*—Louise N. Leary
(74) *Attorney, Agent, or Firm*—Dunlap, Codding & Rogers, P.C.

(57) ABSTRACT

A rapid method for detecting the presence or absence of coliform bacteria in a liquid or liquified dairy sample, for example, skimmed milk, lowfat milk, or whole milk. A growth medium containing a fluorogenic substrate is combined with the dairy sample and is incubated for a brief period of time, for example for about 4 hours, after which a first fluorescence value of 4-methylumbelliferone is measured. The dairy sample is incubated again for about 2–8 hours after which a second fluorescence value of 4-methylumbelliferone is measured. Total, fecal, or thermotolerant coliform bacteria are determined to be present in the sample if the second fluorescent value exceeds the first fluorescent value by a predetermined 4-methylumbelliferone concentration threshold.

23 Claims, No Drawings

RAPID COLIFORM DETECTION SYSTEM

CROSS REFERENCE TO RELATED APPLICATION

This application is a continuation-in-part of U.S. Ser. No. 09/643,437, filed Aug. 22, 2000, now abandoned, which is a continuation of U.S. Ser. No. 09/373,401, filed Aug. 12, 1999, now U.S. Pat. No. 6,165,742, which is a continuation of U.S. Ser. No. 09/143,266 filed Aug. 28, 1998, now U.S. Pat. No. 5,972,641. The specification of each of the above-cited applications is hereby expressly incorporated herein by reference in its entirety.

STATEMENT REGARDING FEDERALLY SPONSORED RESEARCH OR DEVELOPMENT

Not Applicable

BACKGROUND

The present invention relates to rapid methods for detecting microorganisms in products for human consumption or use, and more particularly to rapid methods for detecting the presence or absence of total coliform bacteria, $E.\ coli$ or thermotolerant coliform bacteria in milk or dairy products.

Protection from deleterious microbial contaminants is a global issue. Each year millions of people throughout the world become ill, and thousands die, from contaminated food and water. Disturbing newspaper headlines and stories of epidemic and endemic diseases have increased public awareness of these problems. Testing for bacteria has thus received increasing attention from consumers and public regulatory bodies. In view of this, there is a growing demand for faster methods of detecting microbial contamination. The constant media attention on severe health risks related to microbial contamination of products consumed by humans is leading to increased consumer awareness and public regulatory pressure regarding the safety and the quality of food, water and pharmaceutical products. In addition, economic forces are urging companies to reduce costs by reducing waste, processing time and stock levels.

It is estimated that the industrial market for detection of microbial contaminants was approximately 600 million tests in 1997, amounting to a value of approximately USD 2.5 billion. Of the tests performed annually, the food segment is by far the largest segment, with approximately 310 million tests (53%), followed by the pharmaceutical segment with approximately 200 million tests (32%), the beverage segment with approximately 60 million tests (10%) and finally the environmental segment with approximately 30 million tests (5%). More than 80% of today's testing is performed with slow traditional methods (giving results in 2–3 days), which are laborious and expensive to use. These methods typically use agar plates or standard pour plates (plastic dishes with a nutrient medium), enhancing bacterial growth so that they multiply and their presence can be identified visually as colonies and counted. It is expected that the need for more effective measurements will lead to a significant conversion from slower traditional methods to more rapid and easy to use methods over the next 5 to 10 years. The total market is expected to exceed 800 million tests by 2005, and it is believed that rapid methods will represent 30–40% of the market.

Traditional microbiological methods, which take 18–72 hours to generate results, have led existing regulations to focus on testing of finished products. However, sampling from end product batches for testing does not guarantee that all products in one batch are of good quality. Food processing involves a number of steps and hand-overs (e.g. from the abattoir to the fast food restaurant), giving multiple operations and points for potential microbial carry-over and contamination. The nature of end product testing can therefore not capture every incident of microbial contamination. The ability to rapidly test for contamination at various steps early in a production line would minimize the chances that entire batches of products would have to be destroyed, as is often the case when only end point testing is carried out.

However, with the demand for "just-in-time" deliveries, few companies are able to wait for results of microbial testing. Traditional test methods therefore have value only for historical and documentation purposes. Some producers, however, hold goods until test results are complete, thus raising stock costs. The ability to provide "real time" information for the factories, avoiding contaminated products being shipped, reducing wastage and stocks is therefore desired.

Manufacturers who fail to deliver safe and high quality food products face severe problems, like reduced brand name value, loss or sales, product liability suits and, in worst case, plant closures. The retail industry has increasingly adopted private labels in shelves. The risk of bad publicity and loss of sales in case of "food poisoning" from their branded products, leads retailers to request documentation or testing and implementation of microbial quality control systems from their suppliers. This puts pressure for increased quality control throughout the entire product chain, from delivery of raw materials, through processing, to the end-products.

Over the last 20 years, some new and "easy to use" methods (such as COLILERT and 3M PETRIFILM) have been introduced and have gained approximately 15% of the total market today. These methods are different from the traditional methods in that they have made daily laboratory work easier by reducing many of the practical steps operators take when conducting microbial tests. However, the detection time for these methods, although down from 2–3 days, is still about one day. This is still too long for products that are finished and already shipped to customers. These new tests have therefore not significantly altered how and where companies perform their routine tests.

COLILERT is a 24 hour growth-based method for detection of coliforms/$E.\ coli$ in drinking water. The product has gained widespread usage in the U.S. PETRIFILM, by 3M, represents another product targeted at making microbiology measurements easier to do for workers. Petrifilm is similar to traditional methods regarding time to results and reading of results but eliminates or minimizes sample and media preparations. This is an advance and makes results much more consistent.

Also, in the last 3–4 years, a new class of rapid tests for microbial contamination has managed to gain a market share of approximately 5%, amounting to 30 million tests. Food processing plants must routinely stop production to clean and sanitize the facility. In many plants this occurs during the night, before the plant begins production in the morning. Plant quality control analysts have been perplexed about how to determine if the plant is properly sanitized.

An effective HACCP (Hazard Analysis Critical Control Point) program is dependent upon access to rapid and easy-to-use sanitation screening tests, especially in early states in the production process.

Healthy animals carry pathogens for humans in their intestines and on their hide and hooves. Slaughter unavoidably disseminates these pathogens to the carcass. Excision is considered the most effective bacterial sampling method, but in red meat processing facilities excision is neither practical nor acceptable. Consequently a more practical, non-destructive, and rapid method for carcass bacterial sampling must be validated. These factors should be accomplished without significantly affecting the total sum of recovered bacteria.

The purpose of microbial testing is mainly to identify the presence and risk of presence of bacteria dangerous to the human body. In many cases the level of contamination must also be measured, and in certain cases the microbes must be identified. Microbial tests typically cover either one specific bacterium, or a limited spectrum of bacteria. They are also often limited to testing of specific substances (e.g. water, milk, meat, surfaces).

Specific pathogens are difficult and time-consuming to detect, often taking several days. Hence, indicators of the presence of pathogens, such as coliforms are preferred for analysis and monitoring of water and food quality.

Indicator testing for Total Viable Organisms (referred to TVO or TVC) and coliforms are the most widely used tests for routine monitoring of microbial contamination. Microbial testing and technology requirements vary widely across industries.

The environmental industry segment is concerned with the monitoring of water quality in drinking water, and bathing water (e.g., spas and swimming pools) manufacturing process water, and ambient/recreational water. The global market consists of approximately 30 million tests, mainly for coliforms/$E.$ $coli$ in drinking water. Routine testing of drinking water has traditionally been enforced by stringent public regulatory requirements in every country.

The non-alcoholic beverage industry consists of the bottled water, stilled soft drinks, carbonated soft drinks, and beer production segments. The majority of coliform tests in the beverage industry are performed on bottled water. Larger bottled water producers acknowledge that more rapid results would help them reduce stock levels and potential costs related to calling back shipped products.

The food processing industry consists of a number of products, including milk and dairy products, meat, fish agriculture and multiple food manufacturing products, with different regulatory and company requirements for microbial testing. The industry currently demands a range of technologies to accommodate its testing needs, comply with new regulations, enhance food safety and reduce costs associated with laboratory testing, processing times and stock levels.

Standard testing procedures in the milk industry currently include the following:

(1) International Dairy Federation (IDF) 73A:1985, Milk and Milk Products, Enumeration of coliforms—colony count technique and most probable number at 30° C;

(2) International Standard, ISO, 5541/1 Milk and milk products, Enumeration of coliforms—Part 1: Colony count technique and most probable number at 30° C. First ed. 1986-12-01;

(3) International Standard, ISO, 5541/2 Milk and milk products, Enumeration of coliforms—Part 2: Most probable number at 30° C. First ed. 1986-12-01; and (4) International Standard, ISO, 11866/3 Milk and milk products, Enumeration presumptive *Escherichia coli*— Part 3: Colony count technique at 44° C. using membranes. First ed. 1997-02-15.

Unfortunately, these methods generally take at least 48 to 72 hours to obtain results.

The pharmaceutical industry performs approximately 200 million tests annually and requires the highest standard of microbial quality. Pharmaceutical producers are seeking better control of incoming raw materials, processing stages and final products.

The food service industry (such as caterers and fast food restaurants) is pushing suppliers to document quality of delivered products. Today routine bacteria tests are mostly performed at external laboratories. However, there is reason to believe that recent severe incidents of microbial contamination, leading to food-born disease outbreaks and fatalities have lead the food service industry to reevaluate its quality assurance systems. It is believed that giving caterers the possibility of near-real-time test for specific bacteria indicators like coliforms (as opposed general tests which detect ATP), in the form of a simple instrument test would help companies secure the quality of their sanitation process and incoming products.

As evident from the above, there continues to be a need for methods which will rapidly detect the presence of total coliform bacteria, thermotolerant (including fecal) coliform bacteria or *E. coli* or pathogenic *E. coli* 0-157 in food samples particularly in milk and dairy products.

SUMMARY OF THE INVENTION

In one embodiment, the present invention comprises a direct addition method for rapidly determining the presence or absence of coliform bacteria in a liquid or liquified dairy sample. In this version of the invention, a test sample of milk (e.g. skimmed milk, lowfat milk, whole milk, or cream) or a liquified sample of cheese or yogurt is combined directly with a quantity of growth (culture) medium. The sample is generally not filtered. After a predetermined incubation period, one or more fluorescence measurements of the particular test sample is taken.

The fluorescence measurement is used to determine a concentration of a fluorescent product (e.g., 4-methyl-umbelliferone) in the test sample after incubation. The amount of the fluorescent product is related to the number of total, fecal or thermotolerant coliform cells in the sample. If the concentration of the fluorescent product equals or exceeds a predetermined threshold level after a period of incubation, it is determined that total, fecal or thermotolerant coliform bacteria are present in the sample (depending on the incubation temperature). If the concentration of the fluorescent product does not exceed the predetermined threshold level, it is determined that total, fecal or thermo-tolerant coliform bacteria are absent from the sample, based on a predetermined definition of presence and absence.

DESCRIPTION OF THE PREFERRED EMBODIMENTS

The present invention comprises rapid methods of detecting bacterial contamination of various liquid and solid food products, in particular, milk products, and of areas used to prepare or process such items, wherein the food product is preferably directly combined with a growth medium having a fluorogenic substrate, then incubated, then evaluated for a fluorescence emission from a fluorescent product (defined herein as a material which emits fluorescence when exposed to a particular excitation wavelength).

The methods described herein rely upon the enzymatic hydrolysis by coliform bacteria of a fluorogenic substrate (e.g., 4-methylumbelliferone-β-D-galactoside and/or 4-methylumbelliferone-β-D-glucuronide) which yields a product (e.g.,4-methylumbelliferone, i.e., "MU") which fluoresces upon exposure to an excitation wavelength of light. The fluorgenic substrate and fluorescent product may be any which functions in accordance with the present invention. The fluorescence emission can be quantified using a standard fluorometer.

In practice, samples are incubated for a particular length of time at a preferred temperature, which in one embodiment is about 39° C.±0.5° C. for from about 4 hours to about 8 hours to about 12 hours to determine presence of total coliforms, about 44.0° C.±0.5° C. for about 4 hours to about 8 hours to about 12 hours to determine presence of thermotolerant coliform cells, about 42° C. for pathogenic *E. coli* cells or in another embodiment, or about 30° C. for up to about 11–12 hours for determining total coliforms. "Total coliform" bacteria are those coliform bacteria which are normally present in the colon or small intestine of humans or animals. "Thermotolerant coliform" bacteria include those coliform bacteria which are generally present in the feces of humans or animals and/or which are tolerant of high incubation temperatures. Both of these groups are used as indicators of sanitary quality. The samples are removed after the predetermined incubation times for either pass/fail or presence-absence results. Presence of coliform bacteria in a water sample, for example, is defined as at least one coliform cell per 100 milliliters. Presence of coliform bacteria in a liquid or liquified dairy product, e.g., milk, is defined herein as at least one coliform cell per 1 milliliter. Preferably, the sample is incubated using an incubator which has a heat transference medium which maintains an intimate physical contact with each container. Examples of such heat transference media are water, oil, and metal, or other conductive solids.

In one embodiment, the invention contemplates a rapid method for determining presence or absence of coliforms in an original unfiltered liquid or liquified sample, e.g., skim milk, comprising the steps of:

(a) combining the original sample with an actuating (growth) medium having a fat emulsifying component and a fluorogenic substrate which when metabolized yields a fluorescent product, preferably 4-methylumbelliferone;

(b) incubating the combined sample and actuating medium mixture at a temperature preferred for incubating total, thermotolerant, or *E. coli* coliform cells, for a predetermined duration;

(c) adjusting the pH of the incubated combined sample to an alkaline pH and irradiating said sample with a predetermined excitation wavelength of light;

(d) measuring a fluorescence value from the irradiated combined sample; and (e) concluding that the original sample is contaminated with the specified bacteria when the fluorescence value equals or exceeds a predetermined threshold value which corresponds to a particular concentration value of the fluorescent product.

In the present invention, the actuating medium comprises a nutrient for supporting metabolism of the live total coliforms, thermotolerant coliforms, or pathogenic *E. coli* cells, an induction agent for inducing an enzyme effective in reacting with the substrate for producing the fluorescent product, and in one embodiment, a surfactant effective in enhancing fluorescence or its production and in another embodiment, bile salts for inhibiting gram positive bacteria and for emulsifying fat in milk products. The induction agent may be lactose or IPTG, for example, the surfactant effective in enhancing fluorescence may be sodium lauryl sulfate or tergitol, the enzyme may be β-D-galactosidase or β-D-glucuronidase, the fluorogenic substrate may be, for example, 4-methylumbelliferone-β-D-galactoside and/or 4-methylumbelliferone-β-D-glucuronide, the latter which uses β-D-glucuronidase as the enzyme for degrading the substrate to 4-methylumbelliferone, and the fluorescent product may be 4-methylumbelliferone. Preferably, the irradiation step uses an excitation wavelength of about 380 nm which causes an emission wavelength of about 450 nm from the fluorescent product. When the pH of the incubated sample is adjusted, the adjustment may be made using NaOH, for example, to a pH of above 9 or more preferably, to a pH of above 11, or above 13.

In all versions of the present invention, the culture or growth medium used in determining if an original liquid or liquified sample is contaminated may comprise an aqueous or dry mixture, 4-methylumbelliferone-β-D-galactoside and/or 4-methylumbelliferone-β-D-glucuronide and growth actuators.

In one embodiment, the composition of the actuating medium for mixing with water or liquid sample may comprise in dry form about 20% to about 25% by weight of a peptone, about 10% to 15% by weight of a yeast extract, about 0.2% to 2% by weight of an enzyme inducer, about 20% to 40% by weight of a salt for maintaining isotonicity, about 20% to 25% by weight of pyruvate, about 0.5% to 10% by weight of bile salts, and optimally, about 0.5% to 4.0% by weight of another detergent. The peptone may be proteose peptone No. 3, for example, the salt may be NaCl and the detergent may be sodium lauryl sulfate or tergitol. As noted above, the medium may further comprise 4-methylumbelliferone-β-D-galactoside and/or 4-methylumbelliferone-β-D-glucuronide as fluorogenic substrates, and the fluorogenic substrates may comprise about 0.1% to 2% by weight of the actuating medium.

It will be understood that any actuating medium is suitable as long as the medium functions in accordance with the present invention.

More particularly, in an especially preferred version, the present invention comprises a method for evaluating the presence or absence of coliform bacteria in a milk or liquid dairy sample. The method may comprise the steps of (1) providing an original test sample comprising a liquid or liquified dairy product such as milk, (2) forming an incubation mixture by combining the test sample with an actuating (culture) medium comprising a fluorogenic substrate capable of being acted on by coliform bacteria to form a detectable fluorescent product, (3) incubating the incubation mixture at an incubation temperature for an initial period of time of from about 2 to about 4 hours, (4) irradiating a first subsample or subportion of the test sample with an excitation wavelength and measuring the fluorescence emitted from the subsample of the test sample and determining a concentration of the fluorescent product in the incubated sample, (5) incubating the test sample for an additional period of time (e.g., 2, 4, 6, 8, 10, or 12 more hours) then taking another subsample from the test sample, and determining a concentration of the fluorescent product thereof, and (6) concluding that coliform bacteria were present in the original test sample when the concentration of the fluorescent product in the second subsample equals or exceeds the concentration of the fluorescent product in the first subsample by a threshold concentration or concluding that coliform bacteria were absent in the original sample when the concentration of the fluorescent product in the second subsample does not exceed the concentration of the fluorescent product in the first sample by a threshold concentration after a maximum incubation period. In this method the first (initial) incubation period is preferably about 4 hours, and the incubation temperature is preferably about 39° C.±0.5° C., wherein the presence or absence of total coliforms is detected. Alternatively, when the incubation temperature is about 44° C.±0.5° C., the method detects the presence or absence of thermotolerant coliform bacteria. A preferred threshold concentration of MU is, for example, 100 ppb of MU. The maximum period of time my be, for example, 6, 8, 10, 12 or 14 hours.

In the method the test sample may be skimmed milk, lowfat milk, whole milk, or cream. The excitation wavelength is preferably about 380 nm and the emission wavelength is about 450 nm. Alternatively, the test sample may be irradiated with any excitation wavelength which is effective in causing fluorescence in accordance with the present invention. The culture medium preferably contains a fat emulsifier, which preferably comprises bile salts. In this method, the test sample is not filtered prior to incubation. The fluorescent product is preferably 4-methylumbelliferone and the fluorogenic substrates preferably comprise at least one of 4-methylumbelliferone-β-D-galactoside and 4-methylumbelliferone-β-D-glucuronide.

EXAMPLES

The following examples are intended to further illustrate methods of the present invention including preferred versions; however, these examples are not to be construed as limitations of this invention.

Example 1

Direct Addition

In one embodiment of this method, a sample of milk (skimmed, lowfat, whole or cream) and a quantity of liquified growth (actuating) medium are combined in a 3:1 ratio. The specific ingredients of the preferred medium used herein are shown in Table 2 (dry weights). The added medium may be liquified as prepared as shown for the medium in Table 1 or 2 or it may be added directly as dry medium to the milk and mixed.

In a preferred version, 15 ml of milk and 5 ml of liquified medium are mixed and disposed in a vial. The sample is then incubated at about 39° C. In alternative embodiments the total mixture may be 10 ml (7.5 ml of milk: 2.5 ml of medium) or 80 ml (60 ml of milk: 20 ml of medium), for example.

After an incubation period of at least about 9 hours, the sample is treated with an alkalizing agent as discussed elsewhere herein and irradiated with an excitation wavelength. A fluorescence measurement is then recorded. If the fluorescence measurement indicates that the sample has a 4-methylumbelliferone (MU) concentration equal to or in excess of about 8 µg/l (8 ppb), the sample is considered to be positive for the presence of coliforms. If the MU concentration is below about 8 µg/l (8 ppb), the sample is considered to be negative for the presence of coliforms. In this embodiment, the milk may have a fat content of from about 0.1% (skim) to about 38% (cream). Other milk products with fat contents within this range are also contemplated by the present invention. Presence of coliforms is defined as being 1 cfu/1 ml.

In a preferred version of the method, the growth medium comprises a fat emulsifier for dispersing the fat in the milk sample to a sufficient degree to enable growth of coliform bacteria associated with the fat globules in the sample. In an especially preferred version the fat emulsifier comprises bile salts.

Example 2

Methods

The following methods and compositions may be used as indicated in the various embodiments of the present invention represented herein.

Filtration

Where a filtering step is used in the method, the sample is filtered in accordance with the membrane filtration procedure published in Section 9222D, of *Standard Methods For the Examination of Waste and Wastewater*, 17th Ed., American Public Health Association, 1989, which is hereby expressly incorporated herein by reference.

Use of Fluorometer

In one embodiment, a TURNER DESIGNS TD-700 fluorometer is used using the following procedures:

Calibration

Calibration should be performed every day. Use the Multi-Optional mode calibration procedures.

Transfer 4 ml of HC solution into square cuvette. Cap vial with parafilm and put it in the water bath for 5–10 minutes. Calibration solution should always be heated to test temperature (e.g. 44.5° C. for FC-test) before calibration.

The TD-700 display shows:
1. Setup
2. Calibration

If not press <ESC> twice.

Press <2> from the setup/cal screen. Take the HC vial out from the water bath. Dry outside of the vial, moisture on the outside will result in error. Add 100 µl 2.5 M NaOH. Cover opening with parafilm and invert vial 3 times. NBI The time from when NaOH is added until the sample is placed in the reading cell, should not exceed 20 seconds. Insert vial into the sample adaptor in the sample chamber. Accept the default value of 800 by pressing <1>. When the sample is set, the TD-700 asks if you want to run a blank. Press <9> for not withdrawing a blank. the calibration is done and measurements can start. Run a HC to check if the rfu is around 800. Also run HC samples during a day to control if there is a drift in the instrument.

Reading Samples

Take out 4 ml sample or take out cuvette from incubator. Add 100 µl 2.5 M NaOH. Cover opening with parafilm and invert vial 3 times, and read sample as described above.

If the TD-700 starts to countdown from 600 during an experiment just hit the <ESC> button.

It will be understood that other fluorometers made be employed in the present method.

In the preferred embodiment, the incubator comprises a metal block with cavities for the sample vials. However, the incubator can be any apparatus, such as a water bath, which can maintain a stable incubating temperature and which has a heat transference medium which maintains an intimate physical contact with the container surface. This includes incubators with liquid media such as water or oil, and block or sink incubators having a solid or metal heat transference medium.

Equipment and Supplies

Equipment and supplies used in the pass/fail or presence-absence tests may include a membrane filtration apparatus, a water bath incubator able to hold a temperature constant about the preferred incubation temperature, actuating media, dilution water (e.g., 0.1% sterile peptone or phosphate buffer), membrane filters (e.g., 0.45 µm with grid), 4-methylumbelliferone-β-D-galactoside (MUGal), sodium lauryl sulfate, tergitol, a fluorometer, a solution of 2.5 M NaOH, sterile incubation tubes, square cuvettes (e.g. 4.5 ml PMMA) and 4-methylumbelliferone (4-MU).

Preparation of Liquid Actuating Media

Rehydrate 23.7 g of an actuating media (examples of compositions shown in Table 1 and Table 2) in 200 ml of sterile water. Add 800 ml of boiling water and stir.

TABLE 1

Actuating Media Composition

| Ingredient | Dry Weight (gm.) |
| --- | --- |
| Proteose peptone no. 3 | 100 |
| Yeast extract | 60 |
| IPTG | 2 |
| NaCl | 150 |
| Pyruvate | 100 |
| Sodium lauryl sulphate or Tergitol | 4 |
| Bile salts | 2 |
| 4-methylumbelliferone-β-D-galactoside | 1 gm |
| 4-methylumbelliferone-β-D-glucuronide | 1 gm |
| total | 420 gm |

TABLE 2

Alternate Actuating Medium Composition

| Ingredients | Dry Weight (gm.) |
| --- | --- |
| Proteose peptone no. 3 | 100 |
| Yeast extract | 60 |
| IPTG | 8 |
| NaCl | 150 |
| Pyruvate | 100 |
| SLS or tergitol | 16 |
| Bile Salts | 40 |
| 4-methylumbelliferone-β-D-galactoside | 4 |

Preparation of Internal Calibration Standard

First prepare a 68.1 µM MU stock solution by dissolving 6 mg of 4 MU in 500 ml of media without MU4-methylumbelliferone-β-D-galactoside. Prepare fresh stock solution each second week. Dilute 1 ml of the stock solution to 250 ml with media to prepare a Working solution (0.27 µM MU). This is used as the calibration standard. Fresh working solution is preferably prepared each week.

Example 3

In an alternate method of the present invention a dairy test sample is prepared as above, by being combined with a liquified actuating medium, in a 3:1 ratio (test sample volume: actuating medium volume). A control dairy sample (known or treated to be absent of coliform or thermotolerant coliform bacteria) is also combined with an actuating medium and is used to determine a "background" fluorescence measurement. A calibration sample is prepared by adding a known amount of the fluorescent product (e.g., methylumbelliferone) to a control dairy sample. The dairy test sample, the control (blank) sample, and the calibration sample are incubated at a predetermined temperature (such as 39° C.) for a predetermined length of time, (e.g., up to 12 hours). In a preferred method, subsamples of the samples are taken after predetermined intervals (e.g., 2, 4, 6, 8, 10 or 12 hours) and concentrations of MU therein are determined using fluorescence measurement techniques as described elsewhere herein. It has been discovered that the fat in milk increases the background fluorescence of a milk sample. For example, whole milk has a higher background fluorescence than skimmed milk. When calibration is done with "whole milk", therefore, fluorescence readings of "skimmed" or "lowfat" milk will appear as "negative fluorescence" readings. This does not affect the ultimate "presence/absence" determination of the test sample since the ultimate result in this embodiment of the method depends on the increase in fluorescence relative to the initial fluorescence reading of the test sample.

If the fluorescence value measured from the test sample increases by more than a predetermined concentration threshold (e.g., a concentration of 100 ppb MU) relative to the initial reading of the test sample, a "presence" result is indicated for the test sample. For example, if the test sample has (1) an initial fluorescence value of 100 ppb MU (e.g., after an initial 4 hours of incubation), (2) a second fluorescence value of 250 ppb MU after 8 total hours (or 6, 10, or 12 hours, for example) of incubation, and (3) the predetermined threshold concentration of MU is 100 ppb, the net difference of 150 ppb MU between the first fluorescence value and the second (or a later) fluorescence value thus exceeds the 100 ppb MU threshold, thereby indicating a "presence" result. If the fluorescence value of the last reading (e.g., taken after a maximum period of incubation, such as 12 hours) does not result in a net difference greater than the predetermined fluorescence threshold, an "absence" result is indicated. The threshold may vary, for example, between 10–200 ppb, depending, for example, on the statistical confidence level that is desired. The incubation temperature may range between 32–44° C.±0.5°, and the samples may be incubated for 4–16 hours, for example.

The present invention is not to be limited in scope by the specific embodiments described herein, since such embodiments are intended as but single illustrations of one aspect of the invention and any functionally equivalent embodiments are within the scope of this invention. Indeed, various modifications of the invention in addition to those shown and described herein will become apparent to those skilled in the art from the foregoing description. Such modifications are intended to fall within the scope of the appended claims.

All patents or publications cited herein are hereby incorporated herein by reference.

What is claimed is:

1. A method for detecting coliform bacteria in a milk or liquid dairy sample, comprising:
   providing a milk or liquid dairy sample;
   forming an incubation mixture by combining the dairy sample with a growth medium comprising a substrate capable of being acted on by coliform bacteria to form a detectable fluorescent product;
   incubating the incubation mixture for an initial period of time;

obtaining a first subsample of the incubation mixture and determining a first concentration of the fluorescent product in the first subsample;

incubating the incubation mixture for an additional period of time;

obtaining a second subsample of the incubation mixture after the additional period of time and determining a second concentration of the fluorescent product in the second subsample; and concluding that coliform bacteria were present in the milk or liquid dairy sample when the second concentration of the fluorescent product equals or exceeds the first concentration of the fluorescent product by a predetermined threshold concentration of the fluorescent product, and that coliform bacteria were absent from the milk or liquid dairy sample when the second concentration of the fluorescent product does not equal or exceed the first concentration of the fluorescent product by the predetermined threshold concentration of the fluorescent product after a maximum incubation period.

2. The method of claim 1 wherein in the step of incubating the incubation mixture for an initial period of time, the initial period of time is from about two to about four hours.

3. The method of claim 1 wherein in the step of incubating the incubation mixture for an additional period of time, the additional period of time is from about 1 hour to about 14 hours.

4. The method of claim 1 wherein in the step of incubating the incubation mixture, the incubation mixture is incubated at a temperature of about 39° C.±0.5° C.

5. The method of claim 1 wherein in the step of incubating the incubation mixture, the incubation mixture is incubated at a temperature of about 44° C.±0.5° C.

6. The method of claim 1 wherein in the step of incubating the incubation mixture, the incubation mixture is incubated at a temperature of about 42° C.∓0.5° C.

7. The method of claim 1 wherein in the concluding step, the coliform bacteria are total coliform bacteria.

8. The method of claim 1 wherein in the concluding step, the coliform bacteria are thermotolerant coliform bacteria.

9. The method of claim 1 wherein in the concluding step, the coliform bacterial are fecal coliform bacteria.

10. The method of claim 1 wherein in the step of providing a milk or liquid dairy sample, the milk or liquid dairy sample is skimmed milk, lowfat milk, whole milk, or cream.

11. The method of claim 1 wherein in the step of determining a first concentration, the fluorescent product is 4-methylumbelliferone.

12. The method of claim 1 wherein in the step of forming an incubation mixture, the substrate is selected from the group consisting of 4-methylumbelliferone-β-D-galactoside and 4-methylumbelliferone-β-D-glucuronide.

13. The method of claim 1 wherein in the step of concluding, the predetermined threshold concentration of the fluorescent product is in the range of from 10–200 ppb of 4-methylumbelliferone.

14. The method of detecting the presence or absence of total coliform bacteria in a milk or liquid dairy sample, comprising:

providing a milk or liquid dairy sample;

forming an incubation mixture by combining the dairy sample with a growth medium comprising a substrate capable of being acted on by coliform bacteria to form a detectable fluorescent product;

incubating the incubation mixture at a temperature of about 39° C.±0.5° C. for an initial period of time of about 2 hours to about 6 hours;

obtaining a first subsample of the incubation mixture and determining a first concentration of the fluorescent product in the first subsample;

incubating the incubation mixture for an additional 2 hours to about 10 hours;

obtaining a second subsample of the incubation mixture after the additional period of time and determining a second concentration of the fluorescent product in the second subsample; and concluding that total coliform bacteria were present in the milk or liquid dairy sample when the second concentration of the fluorescent product equals or exceeds the first concentration of the fluorescent product by a predetermined threshold concentration of the fluorescent product, and that total coliform bacteria were absent from the milk or liquid dairy sample when the second concentration of the fluorescent product does not equal or exceed the first concentration of the fluorescent product by the predetermined threshold concentration of the fluorescent product after a maximum incubation period.

15. The method of claim 14 wherein in the step of providing a milk or liquid dairy sample, the milk or liquid dairy sample is skimmed milk, lowfat milk, whole milk, or cream.

16. The method of claim 14 wherein in the step of determining a first concentration, the fluorescent product is 4-methylumbelliferone.

17. The method of claim 14 wherein in the step of forming an incubation mixture, the substrate is selected form the group consisting of 4-methylumbelliferone-β-D-galactoside and 4-methylumbelliferone-β-D-glucuronide.

18. The method of claim 14 wherein in the step of concluding, the predetermined threshold concentration of the fluorescent product is in the range of from 10–200 ppb of 4-methylumbelliferone.

19. The method of detecting the presence or absence of thermotolerant coliform bacteria in a milk or liquid dairy sample, comprising:

providing a milk or liquid dairy sample;

forming an incubation mixture by combining the dairy sample with a growth medium comprising a substrate capable of being acted on by coliform bacteria to form a detectable fluorescent product;

incubating the incubation mixture at a temperature of about 44° C.±0.5° C. for an initial period of time of about 2 hours to about 6 hours;

obtaining a first subsample of the incubation mixture and determining a first concentration of the fluorescent product in the first subsample;

incubating the incubation mixture for an additional 2 hours to about 10 hours;

obtaining a second subsample of the incubation mixture after the additional period of time and determining a second concentration of the fluorescent product in the second subsample; and concluding that thermotolerant coliform bacteria were present in the milk or liquid dairy sample when the second concentration of the fluorescent product equals or exceeds the first concentration of the fluorescent product by a predetermined threshold concentration of the fluorescent product, and that thermotolerant coliform bacteria were absent from the milk or liquid dairy sample when the second concentration of the fluorescent product does not equal or exceed the first concentration of the fluorescent product by the predetermined threshold concentration of the fluorescent product after a maximum incubation period.

20. The method of claim 19 wherein in the step of providing a milk or liquid dairy sample, the milk or liquid dairy sample is skimmed milk, lowfat milk, whole milk, or cream.

21. The method of claim 19 wherein in the step of determining a first concentration, the fluorescent product is 4-methylumbelliferone.

22. The method of claim 19 wherein in the step of forming an incubation mixture, the substrate is selected from the group consisting of 4-methylumbelliferone-$\beta$-D-galactoside and 4-methylumbelliferone-$\beta$-D-glucuronide.

23. The method of claim 19 wherein in the step of concluding, the predetermined threshold concentration of the fluorescent product is in the range of from 10–200 ppb of 4-methylumbelliferone.

* * * * *